Figure 1:
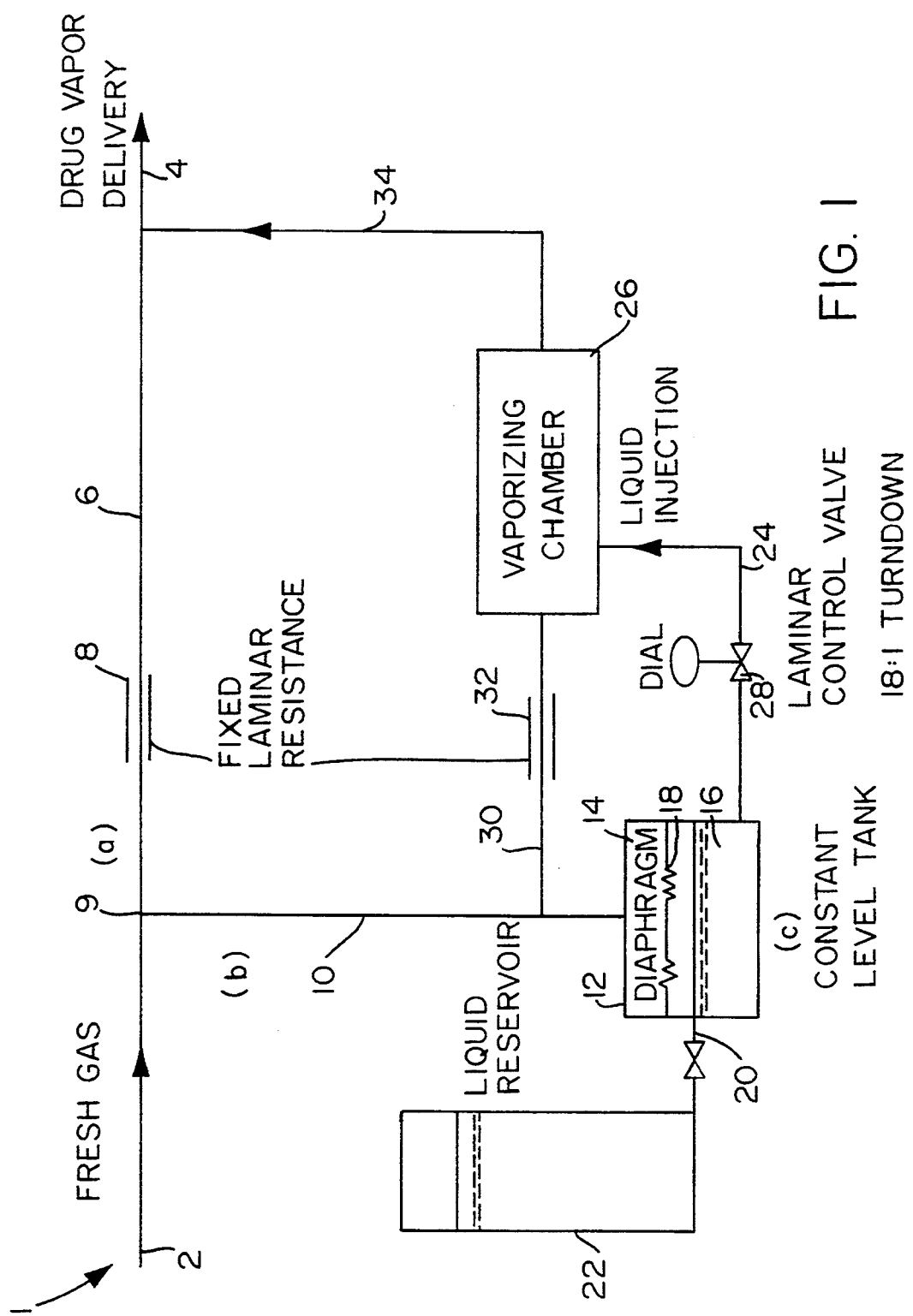

United States Patent [19]
Leach

[11] Patent Number: 5,390,665
[45] Date of Patent: Feb. 21, 1995

[54] ANAESTHETIC VAPORIZER HAVING A PRESSURE SENSITIVE DIAPHRAGM CONNECTING THE ANAESTHETIC RESERVOIR AND VAPORIZING CHAMBER

[75] Inventor: Stuart C. Leach, Ilkley, England

[73] Assignee: The BOC Group plc, Windlesham, England

[21] Appl. No.: 187,372

[22] Filed: Jan. 27, 1994

Related U.S. Application Data

[63] Continuation of Ser. No. 675,846, Mar. 27, 1991, abandoned.

[51] Int. Cl.⁶ .................. A61M 16/10; F16K 11/00; G05D 11/02; F23D 11/00
[52] U.S. Cl. .................. 128/203.25; 128/203.12; 128/203.26; 128/204.25; 128/205.24
[58] Field of Search ............ 128/203.16, 203.17, 128/203.26, 203.27, 204.14, 204.25, 205.11, 203.25, 203.12, 205.24

[56] References Cited

U.S. PATENT DOCUMENTS

| | | | |
|---|---|---|---|
| 1,756,053 | 4/1930 | Colton | 128/203.27 |
| 3,392,753 | 7/1968 | Kleinmann | 137/564.5 |
| 3,841,560 | 10/1974 | Sielaff | 128/203.25 |
| 4,059,657 | 11/1977 | Hay | 128/203.25 |
| 4,129,621 | 12/1978 | Jones et al. | 128/203.25 |
| 4,195,044 | 3/1980 | Miller | 128/203.26 |
| 4,722,334 | 2/1988 | Blackmer et al. | 128/203.26 |
| 4,881,541 | 11/1989 | Eger et al. | 128/203.25 |
| 4,913,140 | 4/1990 | Orec et al. | 128/203.26 |
| 4,942,874 | 7/1990 | Terada et al. | 128/203.26 |

FOREIGN PATENT DOCUMENTS

| | | |
|---|---|---|
| 146220 | 6/1985 | European Pat. Off. |
| 1917774 | 9/1970 | Germany |

Primary Examiner—Kimberly L. Asher
Attorney, Agent, or Firm—Roger M. Rathbun; Larry R. Cassett

[57] ABSTRACT

An anaesthetic vaporizer includes a passageway 10, 30 for directing carrier gas through a fixed laminar restrictor 32 to a vaporizing chamber 26. Liquid anaesthetic agent is injected into the vaporizing chamber 26 from a constant level tank 12 the output of which is controlled by a laminar control valve 28. Liquid anaesthetic agent flow is determined by the pressure of carrier gas in the passageway 10, 30 and the setting of the liquid laminar control valve 28.

5 Claims, 2 Drawing Sheets

5,390,665

ANAESTHETIC VAPORIZER HAVING A PRESSURE SENSITIVE DIAPHRAGM CONNECTING THE ANAESTHETIC RESERVOIR AND VAPORIZING CHAMBER

This is a continuation of application Ser. No. 07/675,846, filed Mar. 27, 1991, now abandoned.

The present invention relates to anaesthetic vaporisers.

UK Patent No 1 224 478, describes an anaesthetic vaporiser of the by-pass type in which a carrier gas such as oxygen, air or nitrous oxide is initially divided on entry to the vaporiser between a first stream which is directed towards the sump or vaporising chamber of the vaporiser to entrain vapour from a volatile liquid anaesthettc contained therein; and a second by-pass stream, the first and second streams subsequently recombining prior to leaving the vaporiser for delivery to a patient.

This known vaporiser has been used successfully over a number of years for delivering anaesthetic agents such as halothane, trichloroethlene and ether derivatives including enflurane, fluoroxene, methoxyflurane and isoflurane. All the aforementioned anaesthetic agents have a boiling point at atmospheric pressure well above 40° C.

However, a new anaesthetic agent has been developed namely 2-(difluoromethoxy)-1,1,1,2-tetrafluoroethane which has a boiling point at atmospheric pressure of between 20° and 25° C. This physical characteristic of 2-(difluoromethoxy)-1,1,1,2-tetrafluoroethane renders existing anaesthetic vaporisers unsuitable for delivering said agent to a patient.

Conventional vaporisers of the by-pass type are unsuitable for this new anaesthetic agent in that its boiling point is approximately in the middle of a conventional vaporisers operating ambient temperature range of between 15° C. and 35° C. When the ambient temperature and hence the vaporiser temperature is above 25° C. heat is transferred to the anaesthetic agent and causes an amount of vapour to boil off such that heat lost by the latent heat of vaporisation is equal to the heat transferred to it.

It is an aim of the present invention to provide an anaesthetic vaporiser which is capable of delivering a predetermined concentration of an anaesthetic agent having a boiling point at normal atmospheric pressure of less than 30° C. to a patient.

According to the present invention, an anaesthetic vaporiser comprises inlet for carrier gas and an outlet for carrier gas and anaesthetic agent for delivery to a patient, a passageway from said inlet to a vaporising chamber and a passage from said vaporising chamber to the outlet, said passageway having located therein a laminar restrictor, and a constant level tank containing liquid anaesthetic agent, a second passage extending between said tank and the vaporising chamber, a laminar control valve being located in said second passage and means for transmitting the pressure in said passageway to the liquid in the liquid level tank to drive the liquid anaesthetic agent along the second passage for injection into the vaporising chamber.

Figure 2:
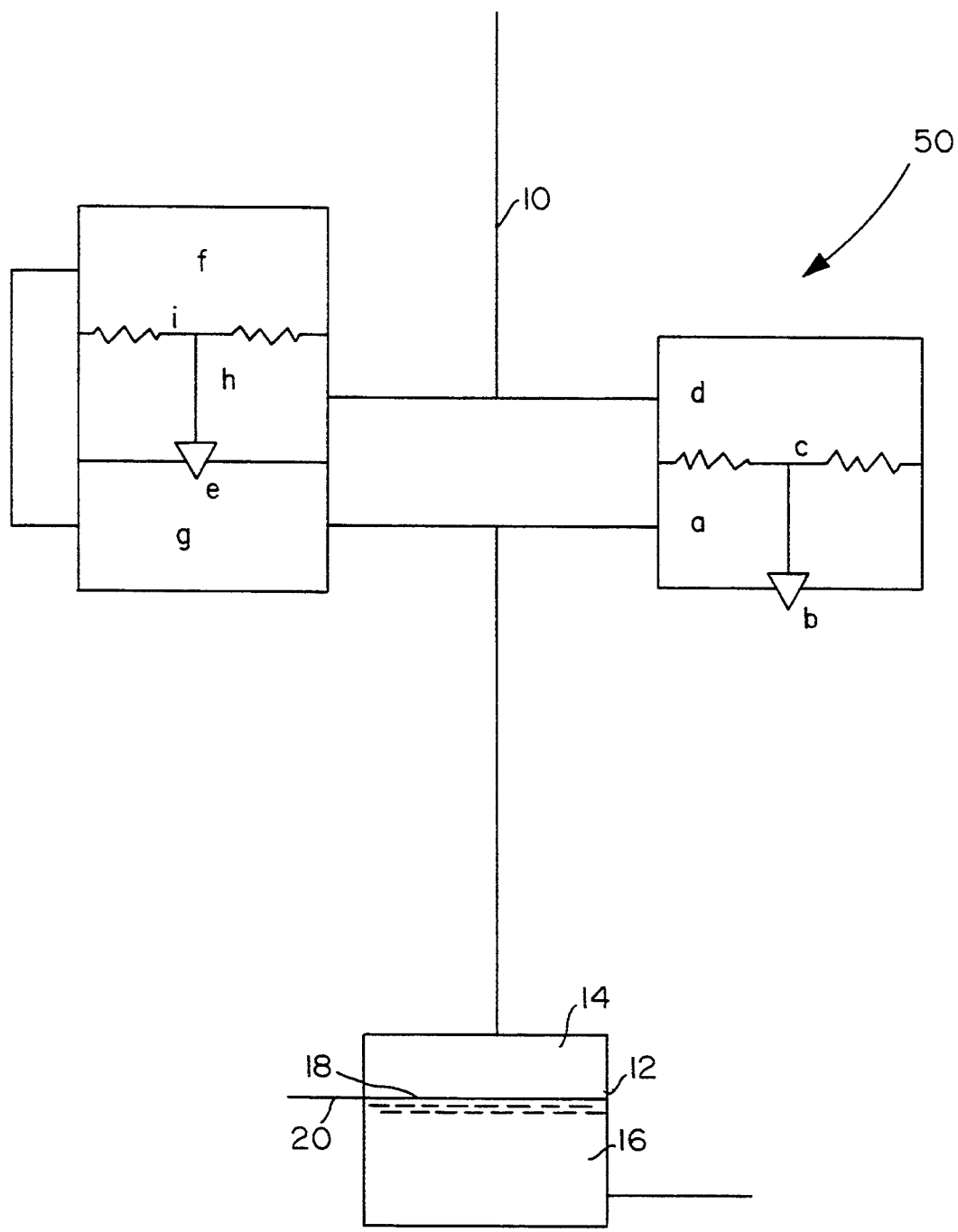

An embodiment of the invention will now be described, by way of example, reference being made to the Figures of the accompanying drawings in which:

FIG. 1 is a diagrammatic sketch of an anaesthetic vaporiser according to the present invention; and FIG. 2 is a diagrammatic sketch of a modification of the anaesthetic vaporiser as illustrated in FIG. 1.

As shown in FIG. 1, an anaesthetic vaporiser 1 has an inlet 2 for carrier gas and an outlet 4 for carrier gas and gaseous anaesthetic agent. Extending between the inlet 2 and the outlet 4 is a passage 6 in which is located a fixed laminar flow restrictor 8. The restrictor 8 exhibits laminar flow characteristics over its operating range.

Extending from the passage 6 from a location 9 upstream of the restrictor 8 is a second passage 10 which communicates with a first chamber 14 of a constant level tank 12. The tank 12 includes a second chamber 16 which is separated from the first chamber 14 by a diaphragm 18.

The second chamber 16 is connected via a passage 20 with a liquid anaesthetic reservoir 22. A further passage 24 extends from the second chamber 16 to a vaporising chamber 26. In the passage 24 between the tank 12 and the vaporising chamber 26 there is located a laminar control valve 28.

A passage 30 extends between the passage 10 and the vaporising chamber 26 and located in the passage 30 is a further fixed laminar restrictor 32. As will be explained, the passages 10, 30 form a passageway for a first stream of carrier gas to flow towards the vaporising chamber 26. Extending from the vaporising chamber 26 to join the passage 6 adjacent the outlet 4 is a passage 34.

In use, fresh carrier gas is fed to the inlet 2 of the vaporiser 1 from a conventional flow metering bank delivering typically 0.2 to 15 liters per minute of air, oxygen or nitrous oxide in various proportions.

The carrier gas enters the vaporiser 1 and at location 9 is divided into a first stream which passes initially along passage 10 and a second by-pass stream which passes along passage 6 through restrictor 8 towards the outlet 4. The proportion of the gas which enters the passages 6 and 10 is determined by the value of the restrictors 8, 32 which have a fixed and linear (laminar) flow characteristic. The carrier gas in the first stream passes from passage 10 into passage 30 through restrictor 32 and into vaporising chamber 26. Within the vaporising chamber 26 volative liquid anaesthetic agent is injected into the vaporising chamber and evaporated into the carrier gas stream. Carrier gas and anaesthetic agent will then leave the vaporising chamber 26 along passage 34 and exit the vaporisor 1 at outlet 4.

It will be evident, that the pressure of the first stream in passages 10, 30 is reflected in the pressure existing in the first chamber 14 and this pressure is transferred across the diaphragm 18 in the constant level tank 12 to liquid contained within the second chamber 16. The temperature of the liquid in the tank 12 is kept sufficiently constant so that variations in temperature hence vapour pressure of the volatile anaesthetic agent are small compared with the pressure of the first stream in passages 10, 30. The liquid level in the second chamber 16 is kept constant and at the same height as the point of injection in the vaporising chamber 26 so that no liquid head effects are superimposed on the pressure available to drive the liquid agent into the chamber 26. The liquid flow from the tank 12 along passage 24 is determined by the pressure in the first stream that is the pressure in passages 10, 30, and the setting of the laminar control valve 28 which is connected to a dial calibrated in percentage volume of drug in the delivered mixture. By use of the laminar characteristics of the fixed restrictors 8, 32 and the laminar control valve 28 the concentration of drug is independent of the carrier gas flow into the vaporiser 1.

With the embodiment illustrated in FIG. 1, as previously stated, it is necessary to maintain the temperature of the liquid anaesthetic agent in the constant level tank 12 constant so that variations in vapour pressure are small compared with the pressure in passages 10, 30.

In practice this is difficult to achieve particularly when heating or cooling is possible with the flow of liquid anaesthetic agent from the reservoir 22 to the tank 12. An alternative approach is illustrated in FIG. 2 in which the passage 10 is interrupted by a balanced venting system 50.

If, for example, the pressure in chamber 14 increases above the pressure in passage 10 due to the heating of the liquid anaesthetic agent, the pressure in chamber a increases to the same value as in chamber 14. This will cause diaphragm c to move upwards (as shown) against the lower pressure in chamber d which is equal to the pressure in passage 10. Movement of the diaphragm c opens a valve b releasing pressure to atmosphere until the pressure imbalance ceases. Conversely, if the pressure in chamber 14 falls relative to the pressure in passage 10 a valve e opens due to the imbalance in pressure between chambers f and h allowing gas to flow from the passage 10 into the chamber g until the imbalance is eliminated.

Means (not shown) is connected between the constant level tank 12 and the reservoir 22 for sensing the level of liquid anaesthetic in the chamber 16 and automatically feeding liquid anaesthetic from the reservoir to the chamber 16 when the liquid level drops below a predetermined level.

Anaesthetic agents such as halothane, enflurane and isoflurane are normally delivered in concentrations of approximately 5% of the total flow of gas administered to a patient. However, the relatively new anaesthetic agent 2-(difluoromethoxy)-1,1,1,2-tetrafluoroethane has a much higher vapour delivery concentration up to, for example, 18% of the total flow of gas administered to a patient. It is an advantage therefore that the laminar control valve 28 be associated with the liquid flow passage 24 rather than the usual line passing gaseous mixture of carrier gas and anaesthetic agent.

In a modification that portion of the passage 6 between the junction 9 and the point where the passage 34 joins the passage 6 can be deleted so that in effect all the carrier gas can be made to pass along the passageway 10, 30 into the vaporising chamber 26.

I claim:

1. An anaesthetic vaporizer which comprises:
   (a) a vaporizing chamber,
   (b) an inlet for carrier gas which is connected to the said vaporizing chamber by means of a passageway,
   (c) an outlet for carrier gas and anaesthetic agent for delivery to a patient which is connected to said vaporizing chamber by means of a first passage,
   (d) a laminar restrictor located in the passageway which connects the inlet to said vaporizing chamber,
   (e) a constant level tank for containing liquid anaesthetic agent which is connected to said vaporizing chamber by means of a second passage,
   (f) a laminar control valve which is located in said second passage, and
   (g) means for transmitting the pressure in the passageway to liquid in the constant level tank and for driving the liquid along the second passage for injection into the vaporizing chamber, said constant level tank including said means for transmitting pressure in the passageway to liquid in the constant level tank, said transmitting means comprising a first and a second chamber, said first chamber and said second chamber separated from one another by a flexible diaphragm, said first chamber in communication with said passageway and transmitting the pressure therefrom across said diaphragm into said second chamber, said second chamber containing the liquid anaesthetic agent in said constant level tank, wherein the pressure transmitted by said diaphragm acts as said means for driving the liquid to said vaporizing chamber.

2. An anaesthetic vaporiser as claimed in claim 1, comprising means for maintaining the level of the liquid anaesthetic agent in the constant level tank constant and at the same level as the point of injection of the liquid anaesthetic agent into the vaporising chamber.

3. An anaesthetic vaporizer as claimed in claim 1, wherein said means for maintaining the liquid level constant in said constant level tank comprises a liquid reservoir connected to the constant level tank.

4. An anaesthetic vaporiser as claimed in claim 1, in which a third passage extends from the inlet directly towards the outlet said third passage including a fixed laminar restrictor and by passing said passageway.

5. An anaesthetic vaporiser as claimed in claim 1, in which the passageway is interrupted by a balanced venting system.

* * * * *